US009422305B2

(12) United States Patent
Cho et al.

(10) Patent No.: US 9,422,305 B2
(45) Date of Patent: Aug. 23, 2016

(54) METHOD FOR PREPARING CURABLE BICYCLIC COMPOUND DERIVED FROM BIOMASS

(71) Applicant: Korea Institute of Industrial Technology, Chungcheongnam-do (KR)

(72) Inventors: Jin Ku Cho, Gyeonggi-do (KR); Sang Yong Kim, Gyeonggi-do (KR); Do Hoon Lee, Seoul (KR); Bo Ra Kim, Daejeon (KR); Baek Jin Kim, Chungcheongnam-do (KR); Jae Won Jung, Seoul (KR); Sang Hyeup Lee, Deagu (KR); Jae Soung Lee, Seoul (KR)

(73) Assignee: Korea Institute of Industrial Technology, Chungcheongnam-do (KR)

( * ) Notice: Subject to any disclaimer, the term of this patent is extended or adjusted under 35 U.S.C. 154(b) by 247 days.

(21) Appl. No.: 14/078,667

(22) Filed: Nov. 13, 2013

(65) Prior Publication Data

US 2014/0066637 A1 Mar. 6, 2014

Related U.S. Application Data

(63) Continuation of application No. 13/394,896, filed as application No. PCT/KR2010/002972 on May 11, 2010, now abandoned.

(30) Foreign Application Priority Data

Sep. 8, 2009 (KR) ........................ 10-2009-0084425

(51) Int. Cl.
*C07D 493/08* (2006.01)
*C08G 59/04* (2006.01)
*A61K 31/06* (2006.01)
*C08F 2/48* (2006.01)

(52) U.S. Cl.
CPC ............. *C07D 493/08* (2013.01); *A61K 31/06* (2013.01); *C08F 2/48* (2013.01); *C08G 59/04* (2013.01)

(58) Field of Classification Search
CPC .............................. C08G 59/04; C07D 493/08
See application file for complete search history.

(56) References Cited

U.S. PATENT DOCUMENTS 5,512,613 A 4/1996 Afzali-Ardakani et al.
6,825,315 B2 11/2004 Aubert
8,039,543 B2 10/2011 Wei et al.

FOREIGN PATENT DOCUMENTS

EP 0 283 951 A1 9/1988
JP 2006193629 A 7/2006

OTHER PUBLICATIONS

Abstract of Article—"Removable Foams Based on an Epoxy Resin Incorporating Reversible Diels-Alder Adducts," McElhanon et al., Journal of applied Polymer Science, vol. 85, Issue 7, Aug. 15, 2002, pp. 1496-1502, 2 pages.
Abstract of Article—"Special-Purpose Epoxy Adhesives," Kochergin et al., Polymer Science Series C, vol. 49, No. 1, 2006, pp. 17-21, 1 pages.
Article—Du et al., "Oxidation of 5-hydroxymethylfurfural to maleic anhydride with molecular oxygen," *Green Chem.*, vol. 13, 2011, pp. 554-557.
Article—Lejemble et al., "From Biomass to Furan Through Decarbonylation of Furfural under Mild Conditions," *Biomass*, vol. 4, 1984, pp. 263-274.
Article—Liu et al., "A Comparative Review of Petroleum-Based and Bio-Based Acrolein Production," *ChemSusChem*, vol. 5, 2012, pp. 1162-1180.
Article—van Putten et al., "Hydroxmethylfurfural, A Versatile Platform Chemical Made from Renewable Resources," *Chem. Rev.*, vol. 113, 2013, pp. 1499-1597.
Search Report for PCT/KR2010/002972 dated Jan. 26, 2011, 2 pages.

*Primary Examiner* — Valerie Rodriguez-Garcia
(74) *Attorney, Agent, or Firm* — Dority & Manning, P.A.

(57) ABSTRACT

The present invention relates to a curable bicyclic compound derived from biomass, solvent-free curable composition and a method for preparing thereof. The curable compound derived from biomass according to the invention comprises a bicycle structure, to which one of two epoxide functional groups are bonded.

4 Claims, No Drawings

METHOD FOR PREPARING CURABLE BICYCLIC COMPOUND DERIVED FROM BIOMASS

CROSS REFERENCE TO RELATED APPLICATION

This application is a continuation of U.S. application Ser. No. 13/394,896, filed on Mar. 8, 2012, which is the national stage entry of International Patent Application No. PCT/KR2010/002972 having a filing date of May 11, 2010, which claims priority to and the benefit of Korean Patent Application No. 10-2009-0084425 filed in the Korean Intellectual Property Office on Sep. 8, 2009, which are incorporated herein in their entirety by reference thereto.

TECHNICAL FIELD

The present invention relates to a curable bicyclic compound derived from biomass, a solvent-free curable composition, and a method for preparing thereof. More specifically, it is suggested to replace materials derived from oil resources used as sources for adhesives or tacky agents, sealant, coating agents and the like with the present invention. The present invention provides a curable compound prepared using a compound derived from biomass instead of petrochemical-derived materials, a solvent-free curable composition and a method for preparing the same.

BACKGROUND ART

Adhesive materials including adhesives, tacky agents, sealant, coating agents, paints and the like are utilized in the industries ranging from civil engineering, architecture to packaging, bookbinding, automobile, electronics, fine chemicals, optics, carpentry, plywood, fabrics, leather as well as for domestic purposes, and their use has indeed become largely extensive. Applications of the adhesive materials include a variety of wood, metal, rubber, plastic, leather, ceramics and so forth, and recently concrete has been added to the above list.

These adhesives which are prepared in the form of a mixture of chemical substances generate toxic substances such as VOC (volatile organic compound), dioxin and endocrine disrupting chemicals due to an organic solvent used in preparing and the diverse volatile additives being added to improve properties. Recently the production and use of these toxic substances are strictly restricted by the international agreement on the environmental regulations. Furthermore, these regulations are used as a novel means of trade sanctions by EU and the like. To keep pace with the current, conventional solvent adhesives are gradually being replaced by those that are water-soluble, solvent-free and hot-melt.

Moreover, while most of the fine chemical materials as well as these adhesive materials are petrochemicals derived from oil refinery process, the global oil price is steadily increasing due to the decrease in its reserves and the surge in demand especially driven by BRICs. As the international agreement strictly regulating greenhouse gas emissions takes effect, it is expected that using irreversible fossil resources such as oil would take great toll on the environment.

Therefore, there are many efforts being made so as to obtain fine chemical products, from instead of oil resources, yet from novel resources onwards, the most typical source to use being carbohydrate biomass. [Ghheda, J. N.; Huber, G. W.; Dumesic, J. A. Angew. Chem. Int. Ed. 2007, 46, 7164-7183, Corma, A.; Iborra, S.; Velty, A. Chem. Rev. 2007, 107, 2411-2502.]

About 170 billion tons of carbohydrate as well as a considerable amount of carbon sources are produced in nature through photosynthesis every year. Humankind however makes partial use of the total carbohydrate and carbon produced for food, paper, furniture, construction materials and so forth. Consequently, the fine chemicals prepared from renewable and sustainable biomass are anticipated to be able to offer alternatives to the petrochemicals. More specifically, how to synthesize a compound containing some sort of adhesiveness or tackiness by using the biomass need further be studied in order to replace curable adhesive materials derived from conventional oil resources.

However, even in case of using these curable compounds derived from renewable and sustainable biomass, curable, particularly, photo-curable adhesive materials containing an acrylate-based or isocyanate-based functional group still have a problem of causing large contraction due to the rapid curing rate, since they generally carry a rapid-curing property at a room temperature through a radical polymerization. Due to the excessive contraction, the demand for introducing the materials with low contraction ratio after curing is currently widespread in the field where adhesive materials are used and especially in those of electronic materials and such where precise dimensional stability is required.

DETAILED DESCRIPTION OF THE INVENTION

Technical Problem

This invention hence aims to solve the problem, wherein the purpose is to prepare a curable bicyclic compound from materials derived from biomass as a basic backbone, so as to replace compounds produced through a petrochemical process. Simultaneously, the present invention may also provide a novel curable compound, which may reduce curing contraction ratio, and a method for preparing thereof with a combination of high yield and cost-effectiveness.

Another purpose of the present invention serves to use as adhesive materials an environmentally friendly solvent-free curable composition comprising the curable compound.

Solution to Problem

This invention intends to solve the technical problem, wherein a curable bicyclic compound derived from biomass according to an embodiment of the present invention having any of the following chemical structures from I to V comprises a bicycle structure as a basic backbone, to which one or two epoxide functional groups are bonded.

[Chemical structure I]

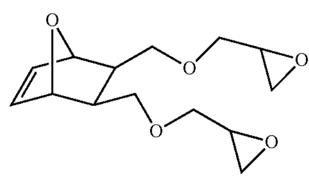

-continued

[Chemical structure II]

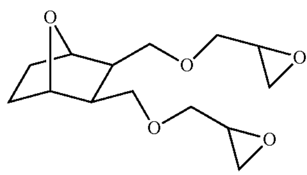

[Chemical structure III]

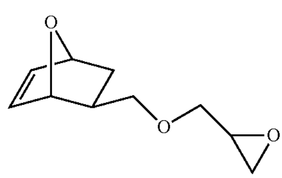

[Chemical structure IV]

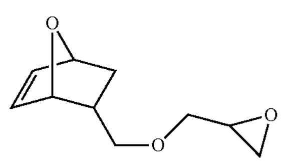

[Chemical structure V]

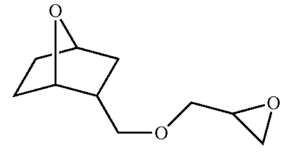

Furthermore, a solvent-free curable composition according to an embodiment of the invention comprises the curable bicyclic compound derived from biomass and an initiator or curing agent.

It is desirable that the initiator herein be a cationic curing initiator.

A method for preparing a curable bicyclic compound derived from biomass according to an embodiment of the invention comprises, a step of preparing a starting material wherein maleic anhydride and furan are prepared as a starting material using respectively cellulose and hemicellulose extracted from carbohydrate biomass; a step of reacting intermediately the maleic anhydride and the furan derived from biomass through Diels-Alder reaction and consecutive reduction to form an intermediate compound comprising bicycle and two alcohol functional groups; and the step of reacting finally the intermediate compound and an epichlorohydrin to produce a compound comprising bicycle and two epoxide functional groups.

It is desirable that the step of reacting intermediately herein further comprise a step of reducing by hydrogenation wherein a second intermediate compound is prepared by hydrogenating reduction of the intermediate compound formed, and the step of reacting finally be to react the second intermediate compound and the epichlorohydrin.

In addition, the method for preparing a curable bicyclic compound derived from biomass according to other embodiments of the invention comprises, a step of preparing a starting material wherein furan is prepared as a starting material using hemicellulose extracted from carbohydrate biomass; a step of reacting intermediately the furan and the methyl acrylate through Diels-Alder reaction and reduction to form an intermediate compound comprising an alcohol functional group and bicycle; and a step of reacting finally the intermediate compound and an epichlorohydrin to produce a compound comprising an epoxide functional group and bicycle.

It is desirable herein that the step of reacting intermediately separate the compounds formed after the Diels-Alder reaction into endo type and exo type compounds respectively, and then conduct reducing the separated compounds respectively.

Preferably, the step of reacting intermediately further comprises a step of reducing by hydrogenation wherein a second intermediate compound is formed by hydrogenating reduction of the intermediate compound formed. It is also desirable that the step of reacting finally be to react the second intermediate compound and the epichlorohydrin.

The step of reacting finally prefers that a mixture comprising the intermediate compound or the second intermediate compound and the epichlorohydrin are reacted using PTC (Phase Transfer Catalyst) as a catalyst in a bi-phasic solvent system where a sodium hydroxide aqueous solution is added.

A method for preparing a solvent-free composition according to an embodiment of the invention comprises a step of preparing a composition wherein a curable adhesive composition is prepared by mixing the curable bicyclic compound derived from biomass prepared by the method for preparing the curable bicyclic compound derived from biomass according to the embodiment of the invention, and cationic curing initiator or curing agent.

Advantageous Effects of the Invention

The present invention may provide an environmentally friendly next-generation curable compound comprising a novel bicyclic compound derived from biomass as a basic backbone as well as a composition containing thereof, which may replace curable materials derived from oil resources.

According to the present invention, a curing material which has a low contraction ratio during curing as compared to that of a conventional radical-type curable material, may be obtained, and a compound applied to such a novel curing material may be prepared with a combination of excellent efficiency and cost-effective synthesis pathway.

BEST MODE FOR CARRYING OUT THE INVENTION

The present invention delves into solutions to those problems, wherein a curable compound derived from biomass according to the invention is an oligomer monomeric structure, and comprises one or two epoxide functional groups bonded to a bicyclic compound.

In other words, this invention intends to replace a bicyclic compound produced through a petrochemical process by preparing a bicyclic compound derived from biomass and applying it as a basic backbone.

Lignin-based biomass, which is most widespread throughout the nature and does not share arable land with food resources, generally contains about 30 to 40% of cellulose and 10 to 20% of hemicellulose. As shown in the following chemical reaction formula 1, the cellulose is extracted to carry out saccharification through hydrolysis or enzymatical treatment under an acid catalyst to obtain a hexose compound. Maleic acid may be obtained by an enzyme process of the hexose compound and successively by dehydration maleic anhydride may be obtained. In addition, furfural may be obtained by reacting the extracted hemicellulose under an acid catalyst and successively through deformylation furan may be obtained.

[Chemical reaction formula I]

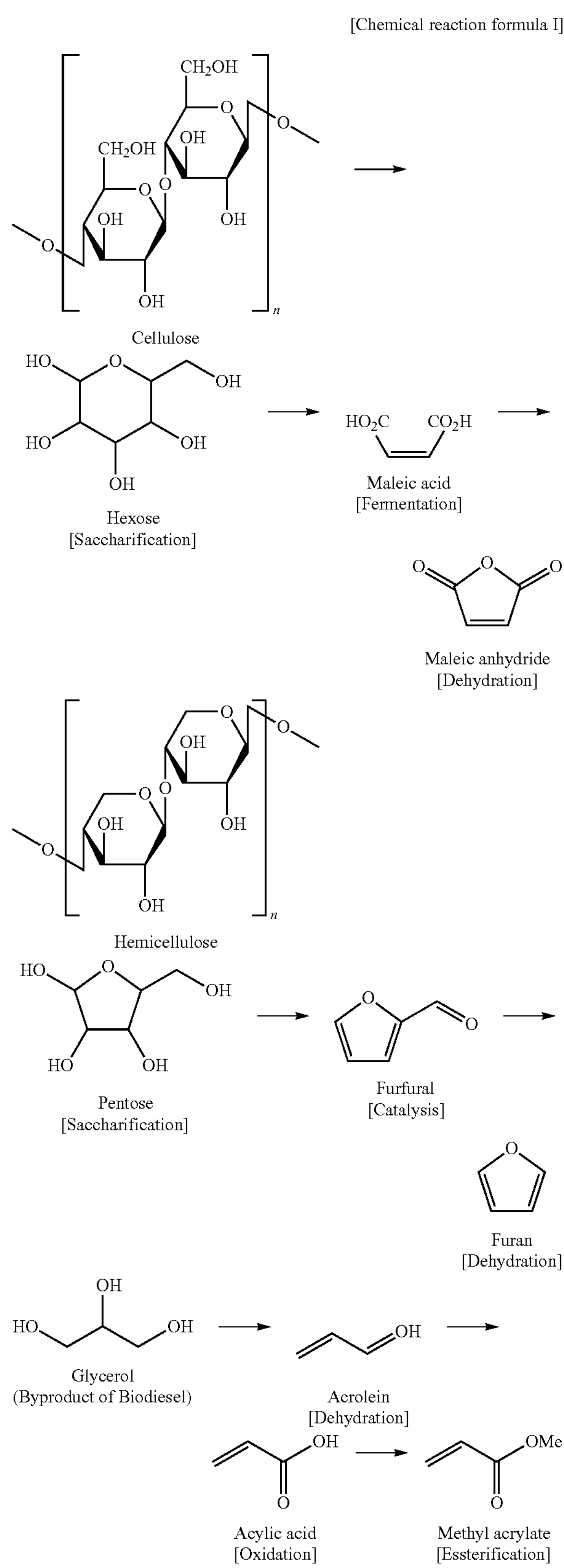

Likewise, the present invention uses a compound derivable from biomass such as furan, maleic anhydride or methyl acrylate, as a starting material. The starting material used in the invention is not particularly restricted if it is capable of forming a structure containing bicycle at the center of a curable compound, which is an end product.

Furthermore, if the furan and the maleic anhydride formed as such have gone through the Diels-Alder reaction and consecutive reduction, a compound containing a bicycle structure as a basic backbone and two alcohol functional groups is obtained as an intermediate. If the furan and the methyl acrylate also have gone through the Diels-Alder reaction and consecutive reduction, a compound (intermediate) containing a bicycle structure as a basic backbone and an alcohol functional group is obtained. In the present invention, the bicycle structure formed from the compounds such as the maleic anhydride and the furan, etc. serves as a basic backbone, and a method for preparing the intermediate product and the end product is to be further described hereinafter.

On the other hand, an epoxide bonded to the bicyclic compound serving as a basic backbone is applied in the invention to increase the degree-of-freedom in molecular structure due to ring-opening reaction of a cyclic molecule, and consequently to decrease in curing contraction ratio. Therefore, the ring-opening reaction of the functional group is induced in a compound (oligomer monomer) by introducing such an epoxide group, so that it prevents drastic contraction of a curing material, thus obtaining a curable compound with significantly reduced curing contraction ratio and a curable composition comprising the compound for adhesive. Since photo curing of the curing material comprising the epoxide functional group is proceeded according to ion mechanism, its feature is that it takes longer to cure compared to acrylic, vinyl-based and styrene-based materials which follow radical curing mechanism, and advantageously has low curing contraction ratio due to the effect of expansion of the molecular structure since the curing is conducted by the ring opening reaction like the ring opening epoxide structure.

The epoxide is an intermediate useful in three-dimensionally regulated synthesis of a complex organic compound due to the diversity of compounds which may be produced by the opening reaction. For example, α-amino alcohol may be obtained simply by ring-opening the epoxide to form an azide ion, and by reducing (for example, hydrogenation) the α-azide alcohol formed. The reaction of other nucleophiles produces a functionalized compound which may be converted to likewise useful materials. If added with Lewis acid, it may operate as an epoxide activator. The epoxide is not known until now about the likelihood of being applied as a curing material in which the epoxide functional group is introduced into the bicyclic compound derived from renewable resources although there are examples of the epoxide used for the adhesives, tacky agents, sealant, coating agents, etc as a functional group of curing material.

Therefore, according to the present invention, by introducing the epoxide into the bicyclic compound derived from renewable resources as the functional group of curing material and thereby replacing chemical products derived from petrochemicals, it may be possible to overcome the setbacks caused by depletion of oil resources as well as to obtain the curing material with significantly reduced contraction ratio.

In addition, the bicyclic compound derived from biomass according to the invention may be formed by bonding one or two epoxide functional groups to a bicycle structure.

Detailed embodiments of a compound derived from biomass according to the invention have a bicycle structure as a basic backbone, to which one or two epoxide functional groups are bonded as represented in any of chemical structures from I to V below.

[Chemical structure I]

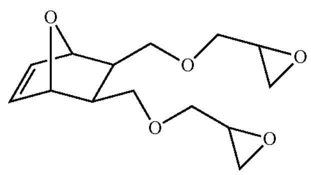

[Chemical structure II]

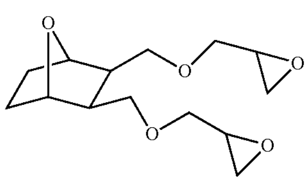

[Chemical structure III]

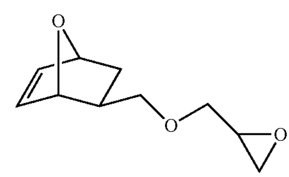

[Chemical structure IV]

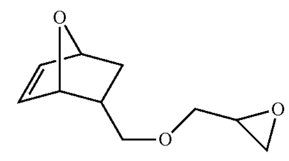

[Chemical structure V]

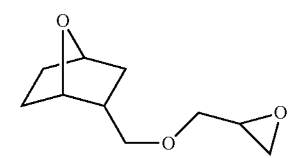

As described in the chemical structures above, the compounds having chemical structures I and II respectively have a bicycle structure as a basic backbone, to which two epoxide functional groups are bonded, whereas the other compounds having the chemical structures from III to V respectively have a bicycle structure as a basic backbone, to which an epoxide functional group is bonded. On the other hand, the compounds having chemical structures I, III, and IV respectively have a central bicycle structure comprising a double bond, whereas the other compounds having chemical structures II and V respectively have a central bicycle structure comprising a single bond only. Furthermore, the compounds having chemical structures IV and V are equal, and represent exo type and endo type respectively.

Maleic acid, furan and methyl acrylate whose synthesis method is described above may preferably be used as a starting material of the compounds having any of the chemical structures from I to V.

The method for preparing the curable bicyclic compound derived from biomass according to the invention is to be described hereinafter.

The method for preparing a curable bicyclic compound derived from biomass basically comprises a step of preparing a starting material, a step of reacting intermediately, and a step of reacting finally. The method is conducted separately in two types of embodiments depending on the starting material.

That is, the method for preparing a curable bicyclic compound derived from biomass according to the first embodiment of the invention uses maleic anhydride and furan as a starting material to obtain compounds (having chemical structures I and II respectively) having a bicycle structure as a basic backbone, to which two epoxide functional groups are bonded, as end products. On the other hand, the method for preparing a curable bicyclic compound derived from biomass according to the second embodiment of the invention uses furan and methyl acrylate as a starting material to obtain compounds (having chemical structures III, IV and V respectively) having a bicycle structure as a basic backbone, to which an epoxide functional group is bonded, as end products.

The methods for preparing a curable bicyclic compound derived from biomass according to each embodiment are to be described below.

The First Embodiment

[Chemical reaction formula 2]

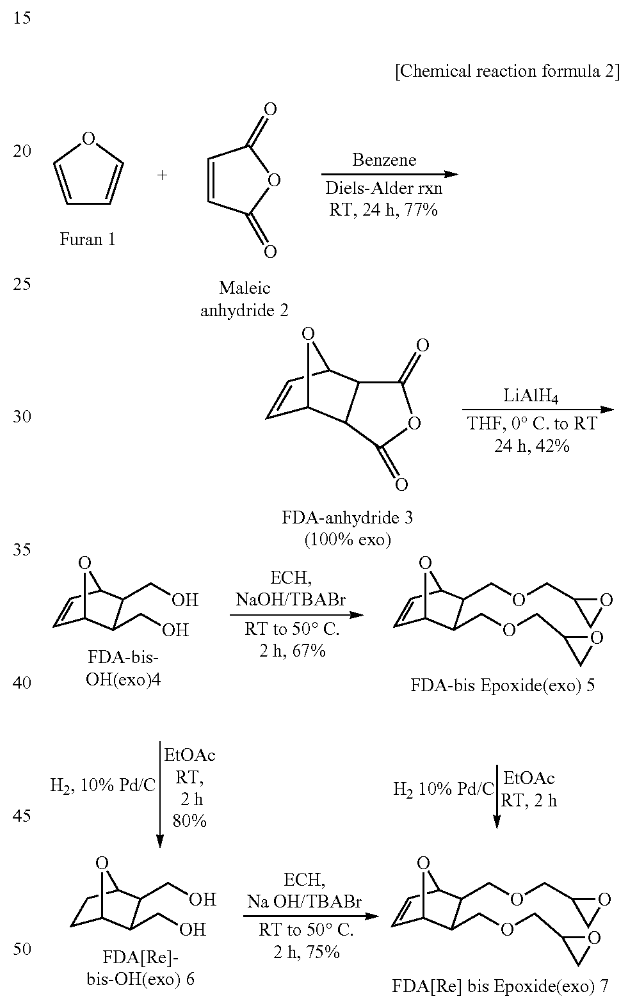

As shown in the chemical reaction formula 2, the method for preparing a curable bicyclic compound derived from biomass according to the first embodiment of the invention comprises, a step of preparing a starting material S10 wherein maleic anhydride 1 and furan 2 are prepared as a starting material, using cellulose and hemicellulose extracted from carbohydrate-based biomass; a step of reacting intermediately S20 the maleic anhydride 1 derived from biomass and the furan 2 through Diels-Alder reaction and consecutive reduction to form an intermediate compound 4 comprising bicycle and two alcohol functional groups; a step of reacting finally S30 the intermediate compound 4 and an epichlorohydrin to produce compounds 5, 7 comprising bicycle and two epoxide functional groups (unillustrated in drawing).

The step of preparing a starting material S10 wherein maleic anhydride and furan are prepared as a starting material herein is not particularly restricted if only the method can prepare the maleic anhydride and furan which are already known, so that an optional method may be used for preparing any type of starting material. For example, as an embodiment of the step of preparing a starting material S10 wherein maleic anhydride and furan are prepared as a starting material, a method for preparing maleic anhydride and furan obtainable from cellulose and hemicellulose extracted from carbohydrate-based biomass is as shown in the chemical reaction formula 1 described above.

The step of reacting intermediately S20 is a step wherein an intermediate compound 4 comprising bicycle and two alcohol functional groups is formed by reacting the maleic anhydride 1 and the furan 2 through Diels-Alder reaction and consecutive reduction.

For example, as shown in chemical reaction formula 2, Furan Diels-Alder-anhydride (hereinafter referred to as 'FDA-anhydride') 3 is synthesized by Diels-Alder reacting the maleic 1 and the furan 2 through recrystallization. The compound (FDA-anhydride), particularly, is obtainable only in the type of exo, which is a thermodynamically stable product. Afterwards, FDA-anhydride 3 is reduced with $LiAlH_4$ in excess to be synthesized as an intermediate compound, 2,3-bis-hydroxymethyl-7-oxabicyclo[2,2,1]hept-5-ene (hereinafter referred to as 'FDA-his-OH') 4 containing two alcohol functional groups and central bicycle in the type of exo.

The step of reacting finally S30 is a step wherein compounds 5, 7 comprising bicycle and two epoxide functional groups are produced by adding an epichlorohydrin (ECH) as a material to introduce an epoxide functional group to the intermediate compound 4 and then stirring.

As a detailed embodiment of the step of reacting finally, it is desirable that a mixture comprising the intermediate compound 4 and the epichlorohydrin be reacted using PTC (Phase Transfer Catalyst) as a catalyst, in a bi-phasic solvent system where a NaOH aqueous solution is added.

PTC may include tetrabutylammonium bromide (TBABr), tetrabutylammonium chloride, tetraoctylammonium chloride, tetrabutylammonium hydrogen sulfate, methyltrioctylammonium chloride, hexadecyltrimethylammonium chloride, hexadecyltrimethylammonium bromide, benzyltrimethylammonium chloride, benzyltriethylammonium chloride, benzyltrimethylammonium hydroxide, benzyltriethylammonium hydroxide, benzyltributylammonium chloride, benzyltributylammonium bromide, tetrabutylphosphonium bromide, tetrabutylphosphonium chloride, tributylhexadecyl phosphonium bromide, butyltriphenylphosphonium chloride, ethyltrioctylphosphonium bromide, tetraphenylphosphonium bromide and so forth, and apart from those above, PTC may not be particularly limited.

It is also desirable that the equivalent weight of epichlorohydrin be from 5 to 20, and more preferably, from 10 to 15.

More specifically, tetrabutylammonium bromide (TBABr) is added as PTC in a bi-phasic solvent system of epichlorohydrin and NaOH aqueous solution, while the intermediate compound is dissolved in a predetermined solvent separately, which is then reacted by slowly adding by drops in the bi-phasic solvent system to synthesize 2,3-bis((oxiran-2-ylmethoxy)methyl)-7-oxabicyclo[2,2,1]hept-5-ene (hereinafter referred to as 'FDA-bis-Epoxide (exo)') 5, which is a novel curing material monomer comprising two epoxide functional groups having chemical structure I in the type of exo.

Furthermore, using the FDA-bis-Epoxide (exo) 5 as a reaction material, through hydrogenating reduction using 10% Pd/C as a catalyst, it is attempted to synthesize 2,3-bis((oxiran-2-ylmethoxy)methyl)-7-oxabicyclo[2,2,1]heptanes (hereinafter referred to as 'FDA[Re]-bis-OH (exo)') 7 having chemical structure II, wherein the double bonding within bicycle of FDA-bis-Epoxide (exo) 5 is reduced. However, the yield is shown to be very low, and as the reaction time takes longer, side reaction is proceeded rapidly. As a consequence of examining the cause of the side reaction, it is verified through documentary survey and NMR analysis that even the epoxide ring itself, whose ring is extremely tense under the condition of the hydrogenating reduction above, goes through the side reaction, in which ring opening hydrogenation reaction is proceeded to be converted to the form of alcohol Therefore, the problem could be overcome by changing the order of the reaction, which is to further comprise a step of reducing by hydrogenation S21 wherein a second intermediate compound, 2,3-bis-hydroxymethyl-7-oxabicyclo[2,2,1]heptanes (hereinafter referred to as 'FDA[Re]-bis-OH (exo)') 6 is prepared by hydrogenating reduction of the intermediate compound 4 obtained from the step of reacting intermediately S20, and to react the second intermediate compound 6 and an epichlorohydrin in the step of reacting finally S30.

More specifically, an intermediate compound FDA-bis-OH (exo) 4 is converted to FDA[Re]-bis-OH (exo) 6 through hydrogenating reduction, which is then reacted with an epichlorohydrin to synthesize FDA[Re]-bis-Epoxide (exo) 7 at over 70% of yield.

The Second Embodiment

[Chemical reaction formula 3]

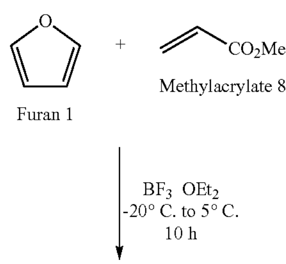

-continued

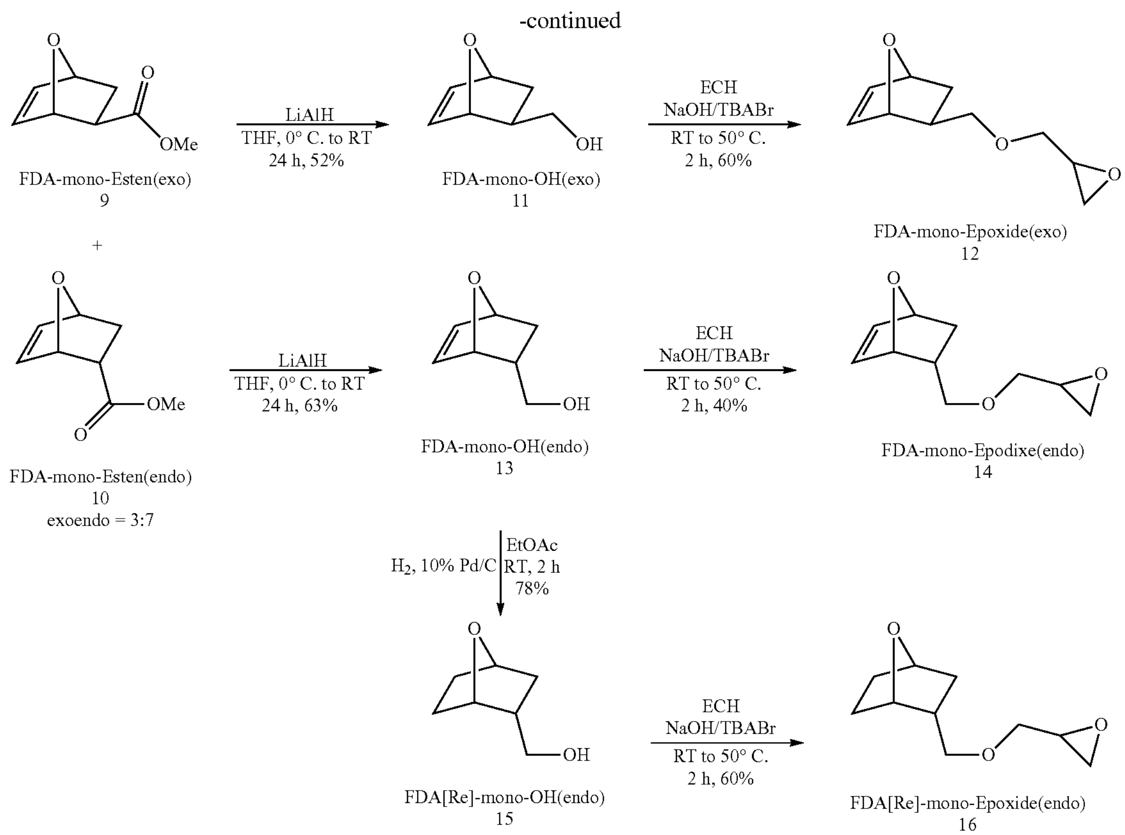

As shown in the chemical reaction formula 3, the method for preparing a curable bicyclic compound derived from biomass according to the second embodiment of the invention comprises, a step of preparing a starting material S100 wherein furan 1 is prepared as a starting material, using hemicellulose extracted from carbohydrate-based biomass; a step of reacting intermediately S200 the furan 1 and methyl acrylate 8 through Diels-Alder reaction and reduction to form intermediate compounds 11, 13 comprising an alcohol functional group and bicycle; a step of reacting finally S300 the intermediate compounds 11, 13 and an epichlorohydrin to produce compounds 12, 14, 16 (i.e. compounds having chemical structure III, IV and V respectively) comprising an epoxide functional group and bicycle.

The step of preparing a starting material S100 is a step wherein the furan equal to the starting material in the first embodiment is prepared, and the step of reacting intermediately S200 is a step wherein the furan 1 and the methyl acrylate 8 are reacted. As for the methyl acrylate 8 herein, as described in the chemical reaction formula 1, it is desirable to use those derived from glycerol produced as byproducts of bio-diesel in a production process.

Moreover, detailed embodiments of the step of reacting intermediately S200 are to be discussed below.

First of all, methyl acrylate 8 and furan 1 as a starting material are reacted through Diels-Alder to be converted to ester compounds 9 and 10 (hereinafter referred to as 'FDA-mono-Ester (exo) 9' and 'FDA-mono-Ester (endo) 10' respectively), which are used to synthesize bicyclic intermediate compounds 11, 13 (hereinafter referred to as 'FDA-mono-OH (exo)' 11 and 'FDA-mono-OH (endo)' 13 respectively) comprising a functional group. Thereby, a mixture of exo type compound and endo type compound is synthesized.

Afterwards, it is desirable to separate the compounds formed from the Diels-Alder reaction into endo type compound and exo type compound respectively, and then to conduct reduction for each of the separated compounds, from which to obtain end products separately.

More specifically, by flash column chromatography for example, the exo and endo type compounds are separated into FDA-mono-Ester (exo) 9 and FDA-mono-Ester (endo) 10 respectively, from which intermediate compounds, FDA-mono-OH (exo) 11 and FDA-mono-OH (endo) 13 are prepared respectively through $LiAlH_4$ reduction.

Through the step of reacting finally S300 afterwards, the intermediate compounds, FDA-mono-OH (exo) 11 and FDA-mono-OH (endo) 13 are reacted with an epichlorohydrin in a bi-phasic solvent system in the presence of PTC to synthesize compounds FDA-mono-Epoxide (exo) 12 and FDA-mono-Epoxide (endo) 14 having chemical structures III and IV respectively.

As in the first embodiment, it further comprises a step of reducing by hydrogenation S201 wherein the intermediate compound 13 prepared by the step of reacting intermediately S200 is reduced by hydrogenation to form a second intermediate compound 15, and a bicyclic compound 16 comprising only a single bonding is obtained by reacting the second intermediate compound 15 and the epichlorohydrin in the step of reacting finally S300.

More specifically, the second intermediate compound, FDA[Re]-mono-OH (endo) 15 comprising an alcohol functional group and a single bonding bicycle may be obtained at almost regular yield by hydrogenating reduction of a double bonding within bicycle structure of the FDA-mono-OH (endo) 13. The FDA[Re]-mono-OH (endo) 15 is then reacted with an epichlorohydrin to synthesize FDA[Re]-mono-Epoxide (endo) 16.

Preparing a Solvent-free Curable Composition

In addition, a solvent-free curable composition may be obtained by comprising and conducting a step of preparing a composition wherein a curable adhesive composition is prepared by adding and mixing the curable bicyclic compound derived from biomass prepared according to the method for preparing a curable bicyclic compound from biomass, and other curable oligomer compounds, initiators such as photo initiator or thermal initiator or curing agent applied in typical epoxy resin composition or other additives. Preferably, the photo initiator or curing agent used in a typical epoxy resin composition is used in order to conduct UV curing as well as photo curing.

In case of conducting photo-initiation, since the curable bicyclic compound derived from biomass according to the invention is a cationic curable (or polymerizable) compound which is polymerized through cationic polymerization and cured, it is desirable to use a cationic photo curing initiator (polymerization initiator) as the curing initiator. As for the cationic curing initiator, those that are able to cationically polymerize the curable bicyclic compound derived from biomass with relative low energy, by generating cationic polymerization initiator which is activated by light irradiation are available for use without restriction. An ionic photoacid-generating photocationic polymerization initiator or nonionic photoacid-generating photocationic polymerization initiator may either be used for the cationic curing initiator. Furthermore, the added quantity of the cationic curing initiator is not particularly limited, which preferably is to be set up appropriately dependent on reactivity or molecular weight of the curable bicyclic compound derived from biomass, or degree of viscoelasticity which is to be given to the curable composition prepared by using the curable bicyclic compound derived from biomass. However, if the added quantity of the cationic curing initiator is too much, curing by light irradiation occurs exceedingly fast since the reactivity of the curable composition grows sharply, which could cause trouble in the following steps. On the other hand, if too little, curing of the curable composition may not be proceeded enough or delay in the curing rate may occur. Therefore, about 0.1 to 15 w %, preferably, 0.2 to 12.5 w % of the added quantity of the cationic curing initiator for the entire curable composition may be added.

The ionic photoacid-generating photocationic polymerization initiator, for example, includes aryldiazoniumn salts, diarylhalonium salts, aromatic sulfonium salts such as triarylsulfonium salts or onium salts such as triphenylphosphonium salts; and organometallic complexes such as iron-arene complex, titanocene complex or arylsilanol-aluminium complex. In addition, the nonionic photoacid-generating photocationic polymerization initiator, for example, includes nitrobenzyl ester, sulfonicacid derivatives, photophate ester, phenolsulfonic acid ester, diazonaphthoquinone or N-hydroxyimidesulfonate, and those may be used alone or combined.

Furthermore, more than one free radical polymerizable compound having more than one ethylentically unsaturated group such as acrylate (i.e. acrylate and/or methacrylate) functional group may be contained in the curable composition in order to compensate rather slow curing rate of the curable bicyclic compound according to the present invention. In case of containing the free radical polymerizable compound in the curable composition, more than one free radical photo initiator may be used along with the above-stated cationic curing initiator as a photo initiator.

Examples of the free radical photo initiator include benzophenone (for example, benzophenone, alkyl-substituted benzophenon or alkoxy-substituted benzophenone); benzoin, for example, benzoin, benzoin ether (for example, bezonin methylether, benzoin ethyl ether and benzoin isopropyl ether), benzoin phenyl ether and benzoin acetate; acetophenone such as acetophenone, 2,2-dimethoxyacetophenone, 4-(phenyltio)acetophenone and 1,1-dichloroacetophenone; benzyl, benzyl ketal (for example, benzyl dimethyl ketal and benzyl diethyl ketal); anthraquinone such as 2-methylanthraquinone, 2-ethylanthraquinone, 2-tert-butylanthraquinone, 1-chloroanthraquinone and 2-amylanthraquinone; triphenylphosphine; for example, benzoylphosphine oxide such as 2,4,6-trimethylbenzoyldiphenylphosphine oxide; thioxantone and xantone, acridin derivatives, phenazine derivatives, quinoxaline derivatives or 1-phenyl-1,2-propanedion-2-0-benzoyloxime, 1-aminophenyl ketone or 1-hydroxyphenyl ketone (for example, 1-hydroxicyclohexyl phenyl ketone, phenyl(1-hydroxyisopropyl) ketone and 4-isopropylphenyl (1-hydroxyisopropyl) ketone), or triazine compound, for example, 4-methyl thiophenyl-1-di(trichloromethyl)-3,5-S-triazine, S-triazine-2-(stilbene)-4,6-bis-trichloromethyl and paramethoxy styryl triazine and so forth, and those may be used alone or combined.

On the other hand, in preparing a solvent-free curable composition according to the invention, a curing agent contained in a typical epoxy resin composition may be used instead of the photo-curable agent. In such a case where the curing agent is used, curing may be conducted in a general manner of using epoxy resin instead of photo curing. Types of the curing agent include amine, acid anhydride, amide or phenol compound. Detailed examples of the curing agent are not limited to but include diaminodiphenylmethane, diethylenetriamine, triethylenetetramine, diaminodiphenylsulfon, isophorondiamine, dicyandiamide, polyamide resin synthesized from linolenic acid dimer and ethylenediamine, phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, phenol novolak and its modifications, imidazole, BF3-amine complex and quinidine derivatives. Such curing agents may be used alone or combined by two or more. In addition, the quantity of the curing agent which may be used for the curable composition of the invention is desirable to be added in accordance with the quantity of the photo initiator stated above.

Aside from those above, the solvent-free curable composition according to the present invention may use a mixture of various additives such as a curing accelerator, an inorganic filler, a release agent and pigment, etc. For example, the curing accelerator may be used along with the curing agent, and detailed examples of the curing accelerator which may be used in the present invention include imidazole such as 2-methylimidazole, 2-ethylimidazole and 2-ethyl-4-methyl-imidazole; tertiary amine such as 2-(dimethylaminomethyl)phenol and 1,8-diaza-bicyclo(5.4.0)-undecane-7; phosphine such as triphenylphosphine; and metallic compound such as octalic stannum. Based on 100 parts of the curable bicycle compound derived from biomass according to the invention is added from 0.01 to 10 parts by weight of the curing accelerator, preferably from 0.2 to 5 parts by weight of the curing accelerator.

The inorganic filler may also be mixed depending on the type of the solvent-free curable composition according to the present invention. Specific examples of the available inorganic filler include silica, alumina and talc. The solvent-free curable composition according to the invention may also contain release agents such as a silane coupling agent, a stearic acid, a palmitic acid, a zinc stearate and a calcium stearate, pigments as well as various mixing additives.

Preferably, the step of preparing a composition may be conducted by fully mixing and homogenizing components of the composition produced as such, for instance, by means of an extruder, a kneader, or a roll, etc.

MODE FOR THE INVENTION

The curable compound derived from biomass according to the invention is to be described with reference to the following preparation examples, experimental example and comparative example.

Preparation Example 1-1 (Preparing FDA-anhydride 3)

Maleic anhydride (20 g, 204 mmol), benzene (100 mL) and furan (15 mL, 205 mmol) are put into a 250 mL round-bottom flask in the presence of argon atmosphere one after another, which then are stirred at a room temperature for 24 hours. It is possible at this point to check that over the course of the reaction, products are precipitated in crystallization to form white slurry. The white slurry is filtered, washed with ether and vacuum dried to obtain FDA-anhydride (27.0 g, 160 mmol, 77% of yield) in the form of white crystallized powder. The data of $^1H$ and $^{13}C$-NMR referring to that is as below.

$^1H$ NMR (400 MHz, $CDCl_3$): δ 6.59-6.57 (m, 2H), 5.47-5.44 (m, 2H), 3.19 (s, 2H).

$^{13}C$ NMR (100 MHz, $CDCl_3$): δ 170.2, 137.2, 137.1, 82.5, 82.4, 48.9

Preparation Example 1-2 (Preparing FDA-bis-OH (exo) 4)

$LiAlH_4$ (6.84 g, 180 mmol) and anhydrous THF (150 mL) are put into a 50 mL round-bottom flask in the presence of argon atmosphere, and then stirred. The dark gray suspension formed is then cooled by ice-bath, into which a compound FDA-anhydride 3 (20 g, 120 mmol) is slowly added by drops after being diluted in anhydrous THF (10 mL). Afterwards the ice-bath is removed from the flask, within which the reaction liquid is reacted by stirring at a room temperature for 24 hours. Upon the completion of the reaction, saturated sodium sulfate aqueous solution is slowly added by drops into the flask, while again using the ice-bath to remove $LiAlH_4$ used in excess. It is possible at this point to check that the reaction liquid in the dark gray suspension state changes to a white slurry form. The reaction liquid is then filtered through the filter laid with celite and washed with a sufficient amount of $CH_2Cl_2$ and $CH_3CN$-EtOAc (1:9) in turn. After moisture from all the collected organic filtrates is removed by $MgSO_4$, the residue having been filtered and vacuum evaporated is separated by flash chromatography (hexanes:EtOAc 4:1) to obtain FDA-bis-OH (exo) 4 (7.738 g, 50 mmol, 42%) in the form of transparent oil. The data of $^1H$ and $^{13}C$-NMR referring to that is as below.

$^1H$ NMR (400 MHz, $CDCl_3$): δ 6.42-6.38 (m, 2H), 4.69 (s, 2H), 3.90-3.73 (m, 4H), 3.63 (s, 2H), 2.02-1.96 (m, 2H).

$^{13}C$ NMR (100 MHz, $CDCl_3$): δ 136.0, 81.5, 81.4, 63.0, 42.7.

Preparation Example 1-3 (Preparing FDA-bis-Epoxide (exo) 5)

Epichlorohydrin (ECH) (474.6 mmol, 33.9 g), NaOH aqueous solution (32.5 g, 407 mmol) of 50% and tetrabutylammonium bromide (TBABr) (1.084 g, 3.37 mmol) are put into a 100 mL round-bottom flask one after another and intensely magnetic stirred. A compound FDA-bis-OH (exo) 4 (5.28 g, 34 mmol) having been diluted in about 30 mL of tetrahydrofuran (THF) is slowly added by drops and intensely stirred at a room temperature for two hours. Afterwards the reaction liquid is moved to a separatory funnel, into which are added distilled water and EtOAc 200 ml each to wash an organic layer twice and washed with saturated NaCI aqueous solution. After moisture in the funnel is removed by $MgSO_4$, the residue having been filtered and vacuum evaporated is separated to flash chromatography (hexanes:EtOAc=1:1→1:2) to obtain FDA-bis-Epoxide (exo) 5 (6.24 g, 23.0 mmol, 67%) in the form of light yellow oil. The data of $^1H$ and $^{13}C$-NMR referring to that is as below.

$^1H$ NMR (400 MHz, $CDCl_3$): δ 6.36 (s, 2H), 4.86 (s, 2H), 3.80-3.72 (m, 2H), 3.67-3.56 (m, 2H), 3.48-3.32 (m, 4H), 3.20-3.13 (m, 2H), 2.84-2.79 (m, 2H), 2.65-2.58 (m, 2H), 1.99-1.90 (m, 2H).

$^{13}C$ NMR (100 MHz, $CDCl_3$): δ 135.7, 80.8, 80.7, 72.4, 71.9, 71.0, 51.0, 50.9, 44.4, 40.1.

Preparation Example 1-4 (Preparing FDA[Re]-bis-OH (exo) 6)

EtOAc (30 mL) is added into a compound FDA-bis-OH (exo) 4 (1.56 g, 10 mmol) in a 50 mL round-bottom flask to be dissolved. 10% Pd-Charcoal catalyst (0.312 g, containing 50% $H_2O$, Degussa type, 10 wt %) is put into the flask, from which air is removed under vacuum. The reaction liquid is then intensely stirred for two hours under 1 atm of hydrogen pressure (by using a balloon). Afterwards, the catalyst is removed by filtering using celite, from which the residue is vacuum evaporated and separated by flash chromatography (EtOAc:$CH_3CN$=7:1) to obtain FDA[Re]-bis-OH (exo) 6 (1.25 g, 8.0 mmol, 80%) in the form of opaque oil. The data of $^1H$ and $^{13}C$-NMR referring to that is as below.

$^1H$ NMR (400 MHz, $CDCl_3$): δ 4.31-4.25 (m, 2H), 3.90-3.76 (m, 2H), 3.72-3.65 (m, 4H), 2.24-2.14 (m, 2H), 1.77-1.69 (m, 2H), 1.58-1.50(m, 2H).

$^{13}C$ NMR (100 MHz, $CDCl_3$): δ 79.8, 62.3, 49.5, 29.8.

Preparation Example 1-5 (Preparing FDA[Re]-bis-Epoxide (Exo) 7)

Epichlorohydrin (ECH) (1.4 mL), NaOH aqueous solution (1.5 g) of 50% and TBABr (100 mg) are put into a 100 mL round-bottom flask one after another and intensely magnetic stirred. A compound FDA[Re]-bis-OH (exo) 6 (700 mg, 4 mmol) having been diluted in about 5 mL of THF is slowly added by drops into the flask and intensely stirred at a room temperature for two hours. Afterwards the reaction liquid is moved to a separatory funnel, into which are added distilled water and EtOAc 200 ml each to wash an organic layer twice and washed with saturated NaCI aqueous solution. After moisture in the funnel is removed by $MgSO_4$, the residue having been filtered and vacuum evaporated is separated to flash chromatography (hexanes:EtOAc=1:1) to obtain FDA[Re]-bis-Epoxide (exo) 7 (870 mg, 3 mmol, 75%) in the form of transparent oil. The data of $^1H$ and $^{13}C$-NMR referring to that is as below.

$^1H$ NMR (400 MHz, $CDCl_3$): δ 4.50-4.36 (m, 2H), 3.80-3.66 (m, 2H), 3.54-3.26 (m, 6H), 3.20-3.08 (m, 2H), 2.88-2.74 (m, 2H), 2.66-2.54 (m, 2H), 2.22-2.08 (m, 2H), 1.80-1.65 (m, 2H), 1.58-1.43 (m, 2H).

$^{13}C$ NMR (100 MHz, $CDCl_3$): δ 79.07, 72.11, 71.76, 70.04, 70.03, 50.94, 50.92, 50.88, 46.36, 44.38, 44.36, 29.53

Preparation Example 2-1 (Preparing FDA-mono-Ester (exo) 9 and FDA-mono-Ester (endo) 10)

Furan 1 (24 g, 352 mmol) and methyl acrylate 8 (10 g, 116 mmol) are put into a 50 mL round-bottom flask in the presence of argon atmosphere, to which a −20° C. of ice-salt bath is installed and then stirred. $BF_3$ etherate (1.5 mL) is slowly added by drops by syringe into the flask, and then stirred in the fridge below 5° C. for 10 hours. After the reaction liquid is moved to a separatory funnel and diluted in EtOAc, an organic layer is washed with distilled water, 5% sodium bicarbonate aqueous solution and saturated NaCl aqueous solution one after another. Moisture in the funnel is then removed by $MgSO_4$, and the residue having been filtered and vacuum evaporated is separated by flash chromatography (hexanes:EtOAc=7:2). EDA-mono-Ester (exo) 9 (4.41 g, 28 mmol, 24%) is obtained from the part eluted later, while from the part eluted first is obtained FDA-mono-Ester (endo) 10 (12.28 g, 79 mmol, 68%) in the form of transparent light yellow oil (exo:endo ratio=3:7) respectively. The data of $^{1}H$ and $^{13}C$-NMR referring to that is as below.

FDA-mono-Ester (exo) 9

$^{1}H$ NMR (400 MHz, $CDCl_3$): δ 6.36-6.33 (m, 2H), 4.97-4.89 (m, 1H), 3.80-3.70 (m, 1H), 3.62 (s, 1H), 2.12 (s, 1H), 1.83-1.80 (m, 2H), 1.41-1.39 (m, 2H).

$^{13}C$ NMR (100 MHz, $CDCl_3$): δ 136.4, 80.2, 80.1, 78.2, 78.1, 77.6, 77.2, 76.9, 65.5, 39.8, 28.3.

FDA-mono-Ester (endo) 10

$^{1}H$ NMR (400 MHz, $CDCl_3$): δ 6.48-6.42 (m, 1H), 6.26-6.20 (m, 1H), 5.20-514 (m, 1H), 5.06-5.00 (m, 1H), 3.70-3.62 (m, 3H), 3.16-3.10 (m, 1H), 2.16-2.08(m, 1H), 1.64-1.58(m, 1H).

$^{13}C$ NMR (100 MHz, $CDCl_3$): δ 172.9, 137.3, 137.2, 132.8, 132.7, 79.3, 79.2, 79.0, 78.9, 52.0, 51.9, 42.9, 28.7

Preparation Example 2-2 (Preparing FDA-mono-OH (exo) 11)

$LiAl_4$ (456 mg) and anhydrous THF (15 mL) are put into a 50 mL round-bottom flask in the presence of argon atmosphere, and then stirred. The dark gray suspension formed is then cooled by ice-bath, into which a compound FDA-mono-Ester (exo) 9 (1.5 g, 9.7 mmol) is slowly added by drops after being diluted in 20 mL anhydrous THF. Afterwards the ice-bath is removed from the flask, within which the reaction liquid is reacted by stirring at a room temperature for 24 hours. Upon the completion of the reaction, saturated sodium sulfate aqueous solution is slowly added by drops into the flask, while again using the ice-bath to remove $LiAlH_4$ used in excess. It is possible at this point to check that the reaction liquid in the dark gray suspension state changes to a white slurry form. The reaction liquid is then filtered through the filter laid with celite and washed with a sufficient amount of $CH_2Cl_2$ and $CH_3CN$-EtOAc (1:9) in turn. After moisture from all the collected organic filtrates is removed by $MgSO_4$, the residue having been filtered and vacuum evaporated is separated by flash chromatography (EtOAc:$CH_3CN$=7:1) to obtain FDA-mono-OH (exo) 11 (0.650 g, 5.1 mmol, 52%) in the form of transparent oil. The data of $^{1}H$ and $^{13}C$-NMR referring to that is as below.

$^{1}H$ NMR (400 MHz, $CDCl_3$): δ 6.36-6.33 (m, 2H), 4.97-4.89 (m, 1H), 3.80-3.70 (m, 1H), 3.62 (s, 1H), 2.12 (s, 1H), 1.83-1.80 (m, 2H), 1.41-1.39 (m, 2H).

$^{13}C$ NMR (100 MHz, $CDCl_3$): δ 136.4, 80.2, 80.1, 78.2, 78.1, 77.6, 77.2, 76.9, 65.5, 39.8, 28.3.

Preparation Example 2-3 (Preparing FDA-mono-OH (endo) 13)

$LiAlH_4$ (852 mg) and anhydrous THF (3 mL) are put into a 50 mL round-bottom flask in the presence of argon atmosphere, and then stirred. The dark gray suspension formed is then cooled by ice-bath, into which the compound FDA-mono-Ester (endo) 10 (3.46 g, 22 mmol) is slowly added by drops after being diluted in 50 mL anhydrous THF. Afterwards the ice-bath is removed from the flask, within which the reaction liquid is reacted by stirring at a room temperature for 24 hours. Upon the completion of the reaction, saturated sodium sulfate aqueous solution is slowly added by drops into the flask, while again using the ice-bath to remove $LiAlH_4$ used in excess. It is possible at this point to check that the reaction liquid in the dark gray suspension state changes to a white slurry form. The reaction liquid is then filtered through the filter laid with celite and washed with a sufficient amount of $CH_2Cl_2$ and $CH_3CN$-EtOAc (1:9) in turn. After moisture from all the collected organic filtrates is removed by $MgSO_4$, the residue having been filtered and vacuum evaporated is separated by flash chromatography (hexanes:EtOAc 1:1.2) to obtain FDA-mono-OH (endo) 13 (1.815 g, 14 mmol, 63%) in the form of transparent oil. The data of $^{1}H$ and $^{13}C$-NMR referring to that is as below.

$^{1}H$ NMR (400 MHz, $CDCl_3$): δ 6.14-6.39 (m, 1H), 6.33-6.29 (m, 1H), 5.02-5.01 (m, 1H), 4.94-4.93 (m, 1H), 3.53-3.50 (m, 1H), 3.17-3.12 (m, 2H), 2.47-2.41 (m, 1H), 2.02-1.95 (m, 1H), 0.72-0.68 (m, 1H)

$^{13}C$ NMR (100 MHz, $CDCl_3$): δ 136.6, 132.3, 79.7, 78.6, 65.0, 40.7, 28.0

Preparation Example 2-4 (Preparing FDA-mono-Epoxide (exo) 12)

Epichlorohydrin (1.5 mL), NaOH aqueous solution (1.5 g) of 50% and TBABr (100 mg) are put into a 100 mL round-bottom flask one after another and intensely magnetic stirred. A compound FDA-mono-OH (exo) 11 (500 mg, 4 mmol) having been diluted in about 5 mL of THF is slowly added by drops into the flask at a room temperature and intensely stirred at a room temperature for two hours. Afterwards the reaction liquid is moved to a separatory funnel, into which are added distilled water and EtOAc 20 ml each to wash an organic layer twice and washed with saturated NaCI aqueous solution. After moisture in the funnel is removed by $MgSO_4$, the residue having been filtered and vacuum evaporated is separated by flash chromatography (hexanes:EtOAc=2.7:1) to obtain FDA-mono-Epoxide (exo) 12 (420 mg, 2.4 mmol, 60%) in the form of transparent oil. The data of $^{1}H$ and $^{13}C$-NMR referring to that is as below.

$^{1}H$ NMR (400 MHz, $CDCl_3$): δ 6.33-6.32 (m, 2H), 4.93-4.92 (m, 1H), 4.88 (s, 1H), 3.80-3.73 (m, 1H), 3.60-3.52 (m, 1H), 3.49-3.36 (m, 2H), 3.19-3.17 (m, 1H), 2.83-2.81 (m, 1H), 2.65-2.61 (m, 1H), 1.91-1.86 (m, 1H), 1.43-1.37 (m, 1H), 1.27-1.22 (m, 1H).

$^{13}C$ NMR (100 MHz, $CDCl_3$): δ 136.0, 135.1, 79.6, 74.5, 72.2, 71.8, 51.0, 44.5, 38.2, 28.6.

Preparation Example 2-5 (Preparing FDA[Re]-mono-OH (endo) 15)

EtOAc (10 mL) is added into a compound FDA-mono-OH (endo) 13 (600 mg, 4.76 mmol) in a 50 mL round-bottom flask to be dissolved. 10% Pd-Charcoal catalyst (120 mg, containing 50% $H_2O$, Degussa type, 10 wt %) is put into the flask, from which air is removed under vacuum. The reaction liquid is then intensely stirred for two hours under 1 atm of hydrogen pressure (by using a balloon). Afterwards, the catalyst is removed by filtering using celite, from which the residue is vacuum evaporated and separated by flash chromatography (EtOAc:hexanes=1:1.2) to obtain FDA [Re]-mono-OH (endo) 15 (595 mg, 4.64 mmol, 97%) in the form of opaque oil. The data of $^1H$ and $^{13}C$-NMR referring to that is as below.

$^1H$ NMR (400 MHz, $CDCl_3$): δ 4.60-4.53 (m, 2H), 3.81-3.75 (m, 1H), 3.59-3.52 (m, 1H), 2.41-2.34 (m, 1H), 1.96-188 (m, 1H), 1.84-1.78 (m, 2H), 1.75-1.70 (m, 1H), 1.68-1.62 (m, 1H), 1.41-1.34 (m, 1H), 0.97-0.92 (m, 1H).

$^{13}C$ NMR (100 MHz, $CDCl_3$): δ 78.4, 77.1, 64.4, 44.5, 34.6, 30.8, 24.4.

Preparation Example 2-6 (Preparing FDA-mono-Epoxide (endo) 14)

Epichlorohydrin (1.5 mL), NaOH aqueous solution (1.5 g) of 50% and TBABr (100 mg) are put into a 100 mL of round-bottom flask one after another and intensely magnetic stirred. A compound FDA-mono-OH (endo) 13 (630 mg, 5 mmol) having been diluted in about 5 mL of THF is slowly added by drops into the flask at a room temperature and intensely stirred at a room temperature for two hours. Afterwards the reaction liquid is moved to a separatory funnel, into which are added distilled water and EtOAc 20 ml each to wash an organic layer twice and washed with saturated NaCI aqueous solution. After moisture in the funnel is removed by $MgSO_4$, the residue having been filtered and vacuum evaporated is separated by flash chromatography (hexanes:EtOAc=2.7:1) to synthesize FDA-mono-Epoxide (endo) 14 (367 mg, 2 mmol, 40%) in the form of transparent oil. The data of $^1H$ and $^{13}C$-NMR referring to that is as below.

$^1H$ NMR (400 MHz, $CDCl_3$): δ 6.38 (dd, J=5.8, 1.2 Hz, 1H), 6.27 (t, J=5.4 Hz, 1H), 5.01 (d, J=2.4 Hz, 1H), 4.93 (d, J=4.8 Hz, 1H), 3.78-3.66 (m, 2H), 3.48-3.25 (m, 2H), 3.16-3.00 (m, 2H), 2.80 (t, J=4.6 Hz, 1H), 2.62-2.46 (m, 2H), 2.04-1.95 (m, 1H), 0.70 (dd, J=11.2, 4.0 Hz, 1H).

$^{13}C$ NMR (100 MHz, $CDCl_3$): δ 136.5, 132.5, 79.7, 78.4, 74.2, 71.9, 51.0, 44.2, 38.0, 28.1.

Preparation Example 2-7 (Preparing FDA[Re]-mono-Epoxide (endo) 16)

Epichlorohydrin (1.5 mL), NaOH aqueous solution (1.2 g) of 50% and TBABr (100 mg) are put into a 100 mL round-bottom flask one after another and intensely magnetic stirred. A compound FDA[Re]-mono-OH (endo) 15 (500 mg, 2.7 mmol) having been diluted in about 5 mL of THF is slowly added by drops into the flask at a room temperature and intensely stirred at a room temperature for two hours. Afterwards the reaction liquid is moved to a separatory funnel, into which are added distilled water and EtOAc 20 ml each to wash an organic layer twice and washed with saturated NaCI aqueous solution. After moisture in the funnel is removed by $MgSO_4$, the residue having been filtered and vacuum evaporated is separated by flash chromatography (hexanes:EtOAc=2.7:1) to synthesize FDA [Re]-mono-Epoxide (endo) 16 (295 mg, 1.6 mmol, 60%) in the form of transparent oil. The data of $^1H$ and $^{13}C$-NMR referring to that is as below.

$^1H$ NMR (400 MHz, $CDCl_3$): δ 4.53-4.50 (m, 2H), 3.79-3.70 (m, 1H), 3.65-3.54 (m, 1H), 3.47-3.30 (m, 2H), 3.14 (s, 1H), 2.80-2.74 (m, 1H), 2.60-2.59 (m, 1H), 2.43-2.42 (m, 1H) 1.91-1.83 (m, 1H), 1.75-1.61 (m, 3H), 1.36-1.34 (m, 1H), 0.94-0.90 (m, 1H).

$^{13}C$ NMR (100 MHz, $CDCl_3$): δ 78.5, 77.6, 77.3, 76.9, 73.1, 71.9, 51.1, 51.1, 44.2, 41.8, 34.6, 30.7, 24.4.

Experimental Example (Measuring Photo Curing Contraction Ratio)

LVDT (Linear Variable Differential Transformer) transducer and UV Spot curing device are used to measure photo curing contraction ratio. This method is to evaluate the curing contraction ratio, using unattached LVDT, which is obtained while photo curing by using the UV-Spot curing device, based on the principle of measuring the linear variations. RB308 Linometer™ of R&B Inc.'s Linometer System is used for the contraction ratio measuring device, and SP-7 of Ushio Inc. is used for the UV-Spot curing device. After a stainless disk is arranged at regular intervals on the unattached linear displacement sensor, which can measure length by using magnetic field, certain thickness or certain amount of sample is loaded on the disk. A slide glass is then spread out over resin and is fixed to the resin. Light source is fixed at a certain height of the slide glass. Afterwards the sensor is operated with UV being irradiated at the same time, allowing the stainless disk to be lifted upwards to the slide glass, and broadening the interval between the sensor and the stainless disk. The interval is recorded to measure the degree of contraction, and the result is shown in the following table 1.

TABLE 1

Photo curing contraction ratio of a curable compound comprising bicycle structure containing an epoxide functional group derived from renewable energy

| Preparation example1 | Sample name | Curing contraction ratio (%) |
|---|---|---|
| Preparation example1 2-4 | FDA-mono-Epoxide(exo)12 | 8.9% |
| Preparation example1 2-6 | FDA-mono-Epoxide(exo)14 | 10.9% |
| Preparation example1 1-3 | FDA-bis-Epoxide(exo)5 | 8.2% |

The curable compound derived from biomass according to the preparation examples of the invention shows efficiency equal to or superior to acrylate-based photo curing materials having generally about 10% of curing contraction ratio in that the curable compound derived from biomass has curing contraction ratio of 8% to 10% as indicated in the table above. Therefore, the curable bicyclic compound derived from biomass according to the invention is considered appropriate to replace a curable compound derived from oil resources as well as to be used in the fields where precise measuring is required such as in the field of electronic materials.

What is claimed is:

1. A method for preparing a curable bicyclic compound derived from biomass, the method comprising:

a step of preparing starting materials furan and maleic anhydride by preparing furan from hemicellulose extracted from biomass and maleic anhydride from cellulose extracted from biomass;

a step of preparing an intermediate compound comprising a bicycle and two alcohol functional groups by reacting the starting materials through Diels-Alder reaction and consecutive reduction; and a step of preparing a curable bicyclic compound comprising bicycle and two epoxide functional groups by reacting the intermediate compound and epichlorohydrin.

2. The method according to claim 1, wherein the reduction at the step of preparing the intermediate compound involves hydrogenation.

3. The method according to claim 1, wherein the step of preparing a curable bicyclic compound involves reacting a mixture comprising the intermediate compound and the epichlorohydrin using PTC (Phase Transfer Catalyst) as a catalyst in a bi-phasic solvent system where a sodium hydroxide aqueous solution is added.

4. The method according to claim 1, wherein the curable bicyclic compound comprising a bicycle and two epoxide functional groups is represented by the following chemical structure I or chemical structure II:

[Chemical structure I]

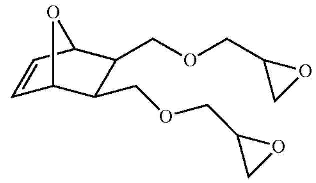

[Chemical structure II]

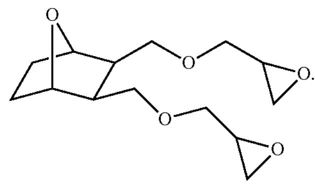

* * * * *